United States Patent [19]

Griep

[11] Patent Number: 5,163,431
[45] Date of Patent: Nov. 17, 1992

[54] ANGIOGRAPHIC CATHETER

[75] Inventor: Wilhelmus A. M. Griep, Roden, Netherlands

[73] Assignee: Cordis Corporation, Miami Lakes, Fla.

[21] Appl. No.: 679,908

[22] Filed: Apr. 3, 1991

[30] Foreign Application Priority Data

Apr. 9, 1990 [NL] Netherlands .................. 9000833

[51] Int. Cl.⁵ .................. A61B 6/00; A61M 25/00
[52] U.S. Cl. .................. 128/658; 604/282
[58] Field of Search .................. 128/656–658; 604/51–53, 204, 280–282

[56] References Cited

U.S. PATENT DOCUMENTS

| 4,735,620 | 4/1988 | Ruiz | 604/281 |
| 4,747,840 | 5/1988 | Ladika et al. | 604/281 |
| 4,842,590 | 6/1989 | Tanabe et al. | 604/282 |
| 4,898,591 | 2/1990 | Jang et al. | 604/282 |
| 4,961,731 | 10/1990 | Bodicky et al. | 604/264 |
| 4,983,169 | 1/1991 | Furukawa | 604/164 |
| 5,045,072 | 9/1991 | Castillo et al. | 604/280 |
| 5,069,673 | 12/1991 | Shwab | 604/280 |

FOREIGN PATENT DOCUMENTS

| 0117093 | 2/1984 | European Pat. Off. |
| 0273618 | 12/1987 | European Pat. Off. |
| 0303487 | 8/1988 | European Pat. Off. |

Primary Examiner—John D. Yasko
Assistant Examiner—Adam J. Cermak
Attorney, Agent, or Firm—Gerstman & Ellis, Ltd.

[57] ABSTRACT

An angiographic catheter which comprises a relatively stiff, tubular, basic catheter body and a less-stiff, tubular, end part connected to one end of the basic body. The end part has a curved form which comprises at least first and second tubular portions, each defining part of the curved form. The first and second tubular portions comprise materials of different stiffness, with the tubular portions being connected to one another in end-to-end relation. Preferably, a straight segment of a first tubular portion is connected in end-to-end relation with the basic catheter body, which catheter body preferably carries a fibrous, tubular reinforcing sheath. Preferably, the stiffness of the material of the tubular portions decreases in the direction extending from the basic body towards the one end.

17 Claims, 1 Drawing Sheet

5,163,431

ANGIOGRAPHIC CATHETER

BACKGROUND OF THE INVENTION

The invention relates to an angiographic catheter comprising a relatively stiff, tubular basic catheter body and a less stiff, tubular end part connected to one end of the basic body. A number of openings are arranged in the wall of the end, part and the catheter distal end also comprises an outlet opening.

As is conventional, during angiographic examination an angiographic catheter is inserted via the blood vessel system of a patient such that the distal end thereof enters the heart and/or the aorta. A contrast fluid can be injected via a central catheter lumen out of the openings, whereby the heart and/or the aorta can be made visible in a radiological laboratory.

When not stressed, the end part naturally has a curved shape which is specifically shaped to accommodate the place where the distal end part of the catheter has to be positioned in the blood vessel system. As the catheter is inserted, the distal end part is kept straightened using a guide wire.

The distal end part must be sufficiently stiff to preserve its curved shape during injection of the contrast fluid. This is of great clinical importance since the correct catheter shape can prevent the catheter from vibrating during injection of the contrast fluid, and moreover prevents the liquid flowing outwardly with force from the openings from damaging the walls of the blood vessels.

However, a stiff, distal end part has the drawback that insertion and withdrawal of the catheter must take place with additionally great care in order to prevent damage to the blood vessels.

The invention has for its object the providing of an angiographic catheter of the type described above, the distal end part of which preserves its shape well during use, but which can still be inserted into and removed from the patient safely.

DESCRIPTION OF THE INVENTION

This is achieved with an angiographic catheter according to the invention where the distal end part is assembled from at least two tube portions of material, each having a different stiffness. The tube portions are connected together at their ends in lengthwise direction. By thus constructing the distal end part from portions of different stiffness, it can be achieved in favorable manner that the portion of the end part which primarily determines its form-retaining capacity during use has a relatively greater stiffness, thus well ensuring this form-retaining capacity, while the distal portion, which potentially can cause the greater risk of damage to the vessel walls, is manufactured from a softer, more flexible material.

In particular, the catheter according to the invention is preferably embodied such that the stiffness of the material of the tubing portions decreases from the direction of the proximal end toward the distal end. The catheter portion defining the distal end, which forms the foremost part of the catheter during insertion of the catheter into the patient, thus has the least stiffness and so the smallest risk of damaging the vessel wall.

The invention is particularly suitable for use in a catheter of the so-called "pigtail" type. The curved shape of the distal end part comprises a straight portion connecting onto the basic catheter body and a curved portion, typically curved substantially through more than 270 degrees in circular manner, connecting to the straight portion.

A catheter of this type is preferably embodied such that a first, relatively stiff tube portion of the end part extends from the basic catheter body to define substantially 180 degrees of the circular curved part, and a second, markedly more flexible, tube portion defines the remaining portion of the curved part, extending to the distal end.

A gradual, typically stepwise, transition in the stiffness is achieved through the material transitions from the basic body to the first tube portion of the end part and then from the first to the second tube portion. It is desirable, in order to be able to manipulate the catheter well, to avoid the presence of sharp ridges between the various joined catheter sections.

The invention is particularly important for thin catheters having a thin wall, i.e. typically catheters having an outer diameter of about 0.05 to 0.06 inch and a wall thickness of about 0.01 to 0.02 inch. Specifically, the outer diameter may be about 0.0540 inch and the inner diameter about 0.0395 inch.

Further advantages and features of the invention will become apparent from the following description with reference to the annexed figures.

DESCRIPTION OF SPECIFIC EMBODIMENTS

Figure 1:
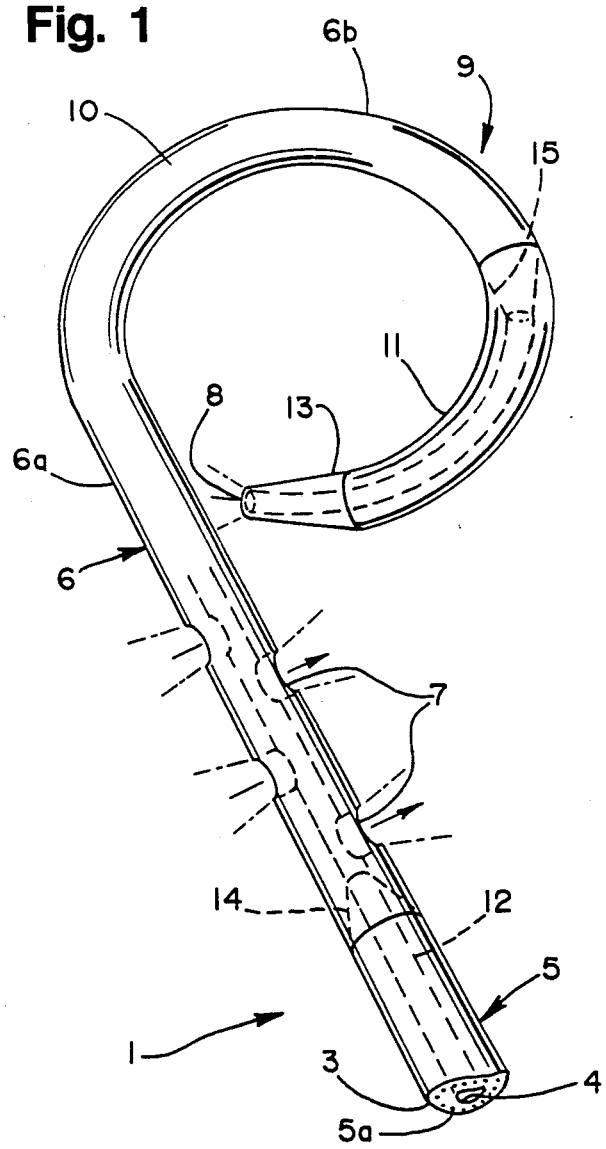
FIG. 1 is a perspective view of the distal portion of a catheter according to the invention.

The catheter 1 shown in FIG. 1 comprises a relatively stiff, tubular basic catheter body 5, only a small portion of which is shown. In the usual manner, a coupling member may be arranged on the proximal end of the basic body 5 (not shown) for connection to a liquid injection device.

The basic catheter body 5 of the catheter 1 comprises an outer layer 3 and an inner layer 4 of a thermoplastic such as nylon. Embedded between these two layers 3, 4 is a conventional reinforcing sheath 5a of braided wire. Basic catheter body 5 is typically of great lengths of many tens of centimeters and with a very small diameter of 0.054 inch, for example. It has suitable properties, such as a sufficient torsional stiffness and pressure resistance in order respectively to be able to insert the catheter into a patient with good control, and during use to pass contrast fluid with considerable pressure into the proximal end of the basic body through the coupling member.

The distal end of the catheter 1 for insertion into the patient comprises an end part 6 which is connected to the basic body 5 and which had no braided sheath. Arranged in the wall of the end part 6 are a number of openings 7, while an end opening 8 is likewise present in the outermost or distal end of the end part 6. These openings 7, 8 communicate with a central lumen 12 in the catheter, through which the contrast fluid can be supplied.

The end part 6 has a curved form, the exact shape of which depends on the desired positioning of the end part during examination of the patient. A catheter of the so-called "pigtail" type is shown in the figures wherein end part 6 comprises a straight portion connecting to the basic body 5 and a substantially circular portion 9, curved substantially through more than 270 degrees, connecting to the straight portion.

As shown, the end part 6 is assembled from a first tube portion 10 and a second tube portion 11. The second tube portion 11 has a lesser stiffness than the first tube portion 10, while the first tube portion 10 has a lesser stiffness than basic catheter body 5. In the preferred embodiment shown, the first tube portion 10 extends from the basic body 5 in a straight segment 6a and then through an arc 6b of substantially 180 degrees. The second end portion 11 extends through the remaining portion of the arc defined by pigtail end part 6.

This embodiment of the end part 6 according to the invention achieves on the one hand that the end part retains its shape well, so that its desired arced shape is preserved well during injection of contrast fluid. The reaction forces resulting from fluid injection have the tendency to "bend out" the curved arc of end part 6. Because the first tube portion 10 is manufactured from a relatively stiff material, these reaction forces are well resisted.

The second tube portion 11 is of much more flexible material than the first tube portion 10. During insertion of the catheter, portion forms the protruding front end of the catheter, and because of its good flexibility the forces exerted on the walls of the blood vessels during insertion do not become so great that the blood vessel wall can suffer damage. When the exerted force increases, the flexible tube portion 11 simply bends to the side.

Specifically, catheter section 10 may have a Shore D durometer of about 70 to 80, specifically about 75. The softer catheter section 11 may have a Shore D durometer of about 50 to 60, particularly about 55. Soft tip 13 may have the same durometer as section 11 since it is typically an integral piece therewith. For example, conventional nylon materials of the above specific softnesses are readily available for catheter manufacture.

The tubular basic catheter body 5 may be made of nylon which has a Shore D durometer of typically about 70 or above, specifically about 75. The nylon or other plastic material from which basic catheter body 5 is made can be stiffer than the plastic material of section 10, if desired, but it is not necessarily made of a stiffer material since the presence of braided wire sheath 5a automatically provides stiffening to basic catheter body 5 even if the plastic material of the basic body is no stiffer than the plastic material of catheter section 10, and even if the plastic material of basic body 5 per se is somewhat less stiff than catheter section 10. Because of the presence of braided wire 5a basic catheter body 5 will tend to have stiffer properties than catheter section 10, 11, while still remaining adequately flexible to provide good functioning as a catheter.

The outermost distal end of the tube portion 11, defining end opening 8, may be given a taper in the usual manner as indicated at 13. This also contributes to reducing the risk of damage.

Figure 2:
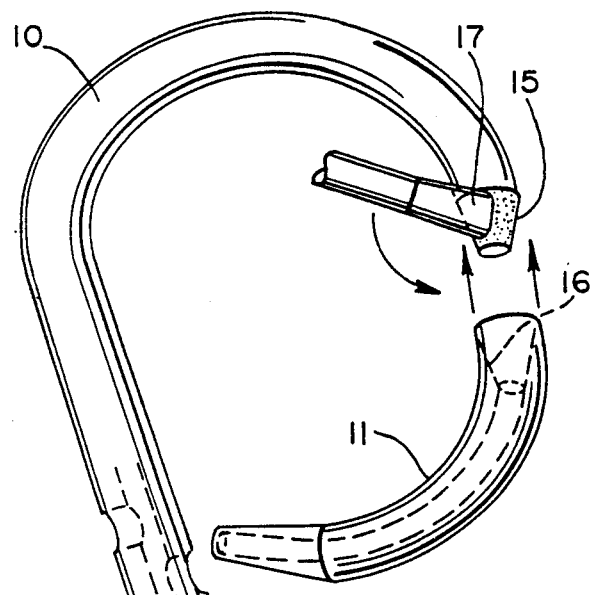
FIG. 2 is a perspective view corresponding with FIG. 1 for elucidation of the method of manufacture thereof.

As indicated by dashed lines at 14, the end part 6 is adhered fixedly to a conically tapered end surface of basic catheter body 5 in a manner similar to that described relative to tube portions 10, 11, which can be connected to each other in similar manner. As FIG. 2 schematically indicates, the end 16 of the first tube portion 10 is tapered. Adhesive may be applied to the surface of end 15, as designated symbolically with the brush 17, and the proximal end 16 of the tube portion 11 is pushed over the tapered surface 15 such that it is connected thereto. Tube portion proximal end 16 may be conically tapered to fit end 15, as is conventional.

FIG. 2 serves only to illustrate the connection of the tube portions 10, 11. In reality, the tube portions will typically already by connected to each other, and the tube 10 will be connected to the basic body 5 before the curved form 8 is imposed therein typically by heat forming. For manufacture, a metal guide wire may be inserted into the central lumen 12, and the various tube portions 5, 10, 11 are pushed over this wire up against each other and adhered fixedly to each other for heat forming and sealing. Thereafter, the outer surfaces of end part 6 are ground smooth. The curved form is arranged therein by plastic deformation, and the openings 7 are punched into the wall.

Instead of adhesive connections, other suitable forms of connection can of course be used, such as ultrasonic welding and the like.

The invention is not limited merely to a catheter of the "pigtail" type having an end part assembled from a pair of portions. Catheters with differently formed end parts can also be embodied in a favorable manner according to the invention, wherein the end parts may also be assembled from more than two tube portions, and the different stiffnesses of the tube portions chosen accordingly.

That which is claimed is:

1. An angiographic catheter of the "pigtail" type comprising a relatively stiff, tubular, basic catheter body and a less-stiff, tubular end part connected to one end of said basic body, wherein said end part has a curved form and comprises at least first and second tubular portions, each defining part of said curved form and comprising materials of different stiffness, said tubular portions being connected to one another in end-to-end relation, said end part comprising a straight portion connecting to the basic catheter body and a curved portion which is curved substantially through more than 270 degrees and connected to the straight portion, and wherein said first tubular portion of the end part extends straight from the basic body and curves through substantially 180 degrees of the curved portion and said second tubular portion extends through the remaining portion of the circular, curved portion.

2. The catheter of claim 1, wherein the stiffness of the material of the tubular portions decreases in the direction from the basic body extending towards the one end.

3. The catheter of claim 2 in which said curved portion is substantially circular.

4. The catheter of claim 3 in which said first tubular portion comprises plastic having a Shore D Durometer of about 70-80, said second tubular portion comprising plastic having a Shore D Durometer of about 50-60.

5. The catheter of claim 4 in which said basic catheter body comprises plastic material having a Shore D Durometer of about 70-80.

6. The catheter of claim 5 in which said basic catheter body carries a fibrous, tubular reinforcing sheath, said first and second tubular portions being free of said sheath.

7. The catheter of claim 1 in which said curved portion is substantially circular.

8. The catheter of claim 1 in which said basic catheter body is connected in end-to-end relation with said first tubular portion of the tubular end part, said first tubular portion comprising plastic having a Shore D Durometer of about 70–80, said second tubular portion comprising plastic having a Shore D Durometer of about 50–60.

9. The catheter of claim 8 in which said basic catheter body comprises plastic material having a Shore D Durometer of about 70–80.

10. The catheter of claim 9 in which said basic catheter body carries a fibrous, tubular reinforcing sheath, said first and second tubular portions being free of said sheath.

11. An angiographic catheter of the "pigtail" type comprising a relatively stiff, tubular, basic catheter body and a less-stiff, tubular, end part connected to one end of said basic body, wherein the end part has a curved form and comprises at least first and second tubular portions, each defining part of said curved form and comprising materials of different stiffness, said tubular portions being connected to one another in end-to-end relation, and in which said basic catheter body is connected in end-to-end relation with said first tubular portion, said first tubular portion comprising plastic having a Shore D durometer of about 70–80, said second tubular portion comprising plastic having a Shore D durometer of about 50–60; said end part comprising a straight portion connecting to the basic catheter body and a curved portion which is curved substantially through more than 270 degrees and connected to the straight portion, and wherein said first tubular portion of the end part extends straight from the basic body and curves through substantially 180 degrees of the curved portion, and said second tubular portion extends through the remaining portion of the curved portion.

12. The catheter of claim 11 in which said curved portion is substantially circular.

13. The catheter of claim 12 in which said basic catheter body comprises plastic material having a Shore D diameter of about 70–80.

14. The catheter of claim 13 in which said basic catheter body carries a fibrous, tubular reinforcing sheath, said first and second tubular portions being free of said sheath.

15. The catheter of claim 12 in which said basic catheter body carries a fibrous, tubular reinforcing sheath, said first and second tubular portions being free of said sheath.

16. The catheter of claim 11 in which said basic catheter body comprises plastic material having a Shore D diameter of about 70–80.

17. The catheter of claim 11 in which said basic catheter body carries a fibrous, tubular reinforcing sheath, said first and second tubular portions being free of said sheath.

* * * * *